US006776796B2

(12) United States Patent
Falotico et al.

(10) Patent No.: US 6,776,796 B2
(45) Date of Patent: Aug. 17, 2004

(54) ANTIINFLAMMATORY DRUG AND DELIVERY DEVICE

(75) Inventors: Robert Falotico, Belle Mead, NJ (US); Gregory A. Kopia, Neshanic, NJ (US); Gerard H. Llanos, Stewartsville, NJ (US); John Siekierka, Towaco, NJ (US); Andrew J. Carter, Portland, OR (US)

(73) Assignee: Cordis Corportation, Miami Lakes, FL (US)

( * ) Notice: Subject to any disclaimer, the term of this patent is extended or adjusted under 35 U.S.C. 154(b) by 129 days.

(21) Appl. No.: 09/850,232

(22) Filed: May 7, 2001

(65) Prior Publication Data

US 2002/0016625 A1 Feb. 7, 2002

Related U.S. Application Data

(63) Continuation-in-part of application No. 09/575,480, filed on May 19, 2000.
(60) Provisional application No. 60/263,979, filed on Jan. 25, 2001, provisional application No. 60/263,806, filed on Jan. 24, 2001, provisional application No. 60/262,614, filed on Jan. 18, 2001, provisional application No. 60/262,461, filed on Jan. 18, 2001, and provisional application No. 60/204,417, filed on May 12, 2000.

(51) Int. Cl.[7] .................................................. A61F 2/06
(52) U.S. Cl. ..................................................... 623/1.46
(58) Field of Search .............................. 623/1.42, 1.43, 623/1.44, 1.45, 1.46

(56) References Cited

U.S. PATENT DOCUMENTS

| | | |
|---|---|---|
| 3,657,744 A | 4/1972 | Ersek |
| 3,932,627 A | 1/1976 | Margraf |
| 4,292,965 A | 10/1981 | Nash et al. |
| 4,441,216 A | 4/1984 | Ionescu et al. |
| 4,503,569 A | 3/1985 | Dotter |
| 4,553,545 A | 11/1985 | Maass et al. |
| 4,580,568 A | 4/1986 | Gianturco |
| 4,613,665 A | 9/1986 | Larm |
| 4,655,771 A | 4/1987 | Wallsten |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,856,516 A | 8/1989 | Hillstead |
| 4,872,867 A | 10/1989 | Joh |

(List continued on next page.)

FOREIGN PATENT DOCUMENTS

| | | |
|---|---|---|
| DE | 3205942 A1 | 9/1983 |
| EP | 540290 A2 | 10/1992 |
| EP | 568 310 A1 | 11/1993 |

(List continued on next page.)

OTHER PUBLICATIONS

Ruef, Johannes Md, et al.; "Flavopiridol Inhibits Smooth Muscle Cell Proliferation In Vitro and Neointimal Formation In Vivo After Carotid Injury In the Rat"; From the Division of Cardiology and Sealy Center for Molecular Cardiology, University of Texas Medical Branch, Galveston; Accepted Apr. 9, 1999; Circulation Aug. 10, 1999; pp 659–665.

Primary Examiner—Manuel Mendez
Assistant Examiner—Mark K. Han
(74) Attorney, Agent, or Firm—Carl J. Evens

(57) ABSTRACT

A drug and drug delivery system may be utilized in the treatment of vascular disease. A local delivery system is coated with rapamycin or other suitable drug, agent or compound and delivered intraluminally for the treatment and prevention of neointimal hyperplasia following percutaneous transluminal coronary angiography. The local delivery of the drugs or agents provides for increased effectiveness and lower systemic toxicity.

11 Claims, 2 Drawing Sheets

U.S. PATENT DOCUMENTS

| | | |
|---|---|---|
| 4,886,062 A | 12/1989 | Wiktor |
| 4,907,336 A | 3/1990 | Gianturco |
| 4,916,193 A | 4/1990 | Tang et al. |
| 4,954,126 A | 9/1990 | Wallsten |
| 4,969,458 A | 11/1990 | Wiktor |
| 4,990,131 A | 2/1991 | Dardik |
| 4,990,155 A | 2/1991 | Wilkoff |
| 4,994,071 A | 2/1991 | MacGregor |
| 5,015,253 A | 5/1991 | MacGregor |
| 5,035,706 A | 7/1991 | Gianturco |
| 5,041,100 A | 8/1991 | Rowland et al. |
| 5,041,126 A | 8/1991 | Gianturco |
| 5,049,132 A | 9/1991 | Shaffer et al. |
| 5,053,048 A | 10/1991 | Pinchuk |
| 5,061,275 A | 10/1991 | Wallsten et al. |
| 5,061,750 A | 10/1991 | Feijen et al. |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,116,365 A | 5/1992 | Hillstead |
| 5,122,154 A | 6/1992 | Rhodes |
| 5,131,908 A | 7/1992 | Dardik et al. |
| 5,133,732 A | 7/1992 | Wiktor |
| 5,134,192 A | 7/1992 | Feijen et al. |
| 5,135,536 A | 8/1992 | Hillstead |
| 5,163,952 A | 11/1992 | Froix |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,180,366 A | 1/1993 | Woods |
| 5,182,317 A | 1/1993 | Winters et al. |
| 5,185,408 A | 2/1993 | Tang et al. |
| 5,192,307 A | 3/1993 | Wall |
| 5,195,984 A | 3/1993 | Schatz |
| 5,213,576 A | 5/1993 | Abiuso et al. |
| 5,217,483 A | 6/1993 | Tower |
| 5,222,971 A | 6/1993 | Willard et al. |
| 5,226,913 A | 7/1993 | Pinchuk |
| 5,234,456 A | 8/1993 | Silvestrini |
| 5,246,445 A | 9/1993 | Yachia et al. |
| 5,258,020 A | 11/1993 | Froix |
| 5,258,021 A | 11/1993 | Duran |
| 5,262,451 A | 11/1993 | Winters et al. |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,283,257 A | 2/1994 | Gregory et al. |
| 5,288,711 A | 2/1994 | Mitchell et al. |
| 5,290,305 A | 3/1994 | Inoue |
| 5,292,331 A | 3/1994 | Boneau |
| 5,292,802 A | 3/1994 | Rhee et al. |
| 5,304,121 A | 4/1994 | Sahatjian |
| 5,304,200 A | 4/1994 | Spaulding |
| 5,306,250 A | 4/1994 | March et al. |
| 5,308,862 A | 5/1994 | Ohlstein |
| 5,308,889 A | 5/1994 | Rhee et al. |
| 5,314,444 A | 5/1994 | Gianturco |
| 5,314,472 A | 5/1994 | Fontaine |
| 5,328,471 A | 7/1994 | Slepian |
| 5,334,301 A | 8/1994 | Heinke et al. |
| 5,336,518 A | 8/1994 | Narayanan et al. |
| 5,338,770 A | 8/1994 | Winters et al. |
| 5,342,348 A | 8/1994 | Kaplan |
| 5,342,387 A | 8/1994 | Summers |
| 5,342,621 A | 8/1994 | Eury |
| 5,354,257 A | 10/1994 | Roubin et al. |
| 5,354,308 A | 10/1994 | Simon et al. |
| 5,356,433 A | 10/1994 | Rowland et al. |
| 5,366,504 A | 11/1994 | Andersen et al. |
| 5,368,566 A | 11/1994 | Crocker |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,299 A | 1/1995 | Fearnot et al. |
| 5,382,261 A | 1/1995 | Palmaz |
| 5,383,928 A | 1/1995 | Scott et al. |
| 5,387,235 A | 2/1995 | Chuter |
| 5,389,106 A | 2/1995 | Tower |
| 5,393,772 A | 2/1995 | Yue et al. |
| 5,395,390 A | 3/1995 | Simon et al. |
| 5,397,355 A | 3/1995 | Marin et al. |
| 5,403,341 A | 4/1995 | Solar |
| 5,405,377 A | 4/1995 | Cragg |
| 5,409,696 A | 4/1995 | Narayanan et al. |
| 5,411,549 A | 5/1995 | Peters |
| 5,415,619 A | 5/1995 | Lee et al. |
| 5,419,760 A | 5/1995 | Narciso, Jr. |
| D359,802 S | 6/1995 | Fontaine |
| 5,421,955 A | 6/1995 | Lau |
| 5,423,885 A | 6/1995 | Williams |
| 5,429,618 A | 7/1995 | Keogh |
| 5,429,634 A | 7/1995 | Narciso |
| 5,439,446 A | 8/1995 | Barry |
| 5,441,515 A | 8/1995 | Khosravi et al. |
| 5,441,516 A | 8/1995 | Wang et al. |
| 5,441,947 A | 8/1995 | Dodge et al. |
| 5,443,458 A | 8/1995 | Eury |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,447,724 A | 9/1995 | Helmus et al. |
| 5,449,372 A | 9/1995 | Schmaltz et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,486,357 A | 1/1996 | Narayanan |
| 5,496,365 A | 3/1996 | Sgro |
| 5,500,013 A | 3/1996 | Buscemi et al. |
| 5,510,077 A | 4/1996 | Dinh et al. |
| 5,516,781 A | 5/1996 | Morris et al. |
| 5,519,042 A | 5/1996 | Morris et al. |
| 5,523,092 A | 6/1996 | Hanson et al. |
| 5,527,354 A | 6/1996 | Fontaine et al. |
| 5,545,208 A | 8/1996 | Wolff et al. |
| 5,551,954 A | 9/1996 | Buscemi et al. |
| 5,554,182 A | 9/1996 | Dinh et al. |
| 5,554,954 A | 9/1996 | Takahashi |
| 5,556,413 A | 9/1996 | Lam |
| 5,562,922 A | 10/1996 | Lambert |
| 5,563,146 A | 10/1996 | Morris et al. |
| 5,569,197 A | 10/1996 | Helmus et al. |
| 5,569,295 A | 10/1996 | Lam |
| 5,569,462 A | 10/1996 | Martinson et al. |
| 5,571,166 A | 11/1996 | Dinh et al. |
| 5,574,059 A | 11/1996 | Regunathan et al. |
| 5,578,075 A | 11/1996 | Dayton |
| 5,580,873 A | 12/1996 | Bianco et al. |
| 5,580,874 A | 12/1996 | Bianco et al. |
| 5,591,140 A | 1/1997 | Narayanan et al. |
| 5,591,197 A | 1/1997 | Orth et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,605,696 A | 2/1997 | Eury et al. |

| Patent | Date | Inventor |
|---|---|---|
| 5,607,463 A | 3/1997 | Schwartz et al. |
| 5,607,475 A | 3/1997 | Cahalan et al. |
| 5,609,629 A | 3/1997 | Fearnot et al. |
| 5,620,984 A | 4/1997 | Bianco et al. |
| 5,621,102 A | 4/1997 | Bianco et al. |
| 5,622,975 A | 4/1997 | Singh et al. |
| 5,624,411 A | 4/1997 | Tuch |
| 5,628,785 A | 5/1997 | Schwartz et al. |
| 5,629,077 A | 5/1997 | Turnlund et al. |
| 5,629,315 A | 5/1997 | Bianco et al. |
| 5,632,763 A | 5/1997 | Glastra |
| 5,632,840 A | 5/1997 | Campbell |
| 5,637,113 A | 6/1997 | Tartaglia et al. |
| 5,643,312 A | 7/1997 | Fischell et al. |
| 5,643,939 A | 7/1997 | Ohlstein |
| 5,646,160 A | 7/1997 | Morris et al. |
| 5,648,357 A | 7/1997 | Bianco et al. |
| 5,649,952 A | 7/1997 | Lam |
| 5,649,977 A | 7/1997 | Campbell |
| 5,651,174 A | 7/1997 | Schwartz et al. |
| 5,652,243 A | 7/1997 | Bianco et al. |
| 5,653,992 A | 8/1997 | Bezwada et al. |
| 5,662,609 A | 9/1997 | Slepian |
| 5,665,728 A | 9/1997 | Morris et al. |
| 5,669,924 A | 9/1997 | Shaknovich |
| 5,670,506 A | 9/1997 | Leigh et al. |
| 5,672,638 A | 9/1997 | Verhoeven et al. |
| 5,674,242 A | 10/1997 | Phan et al. |
| 5,679,400 A | 10/1997 | Tuch |
| 5,679,659 A | 10/1997 | Verhoeven et al. |
| 5,693,085 A | 12/1997 | Buirge et al. |
| 5,697,967 A | 12/1997 | Dinh et al. |
| 5,697,971 A | 12/1997 | Fischell et al. |
| 5,700,286 A | 12/1997 | Tartaglia et al. |
| 5,707,385 A | 1/1998 | Williams |
| 5,709,874 A | 1/1998 | Hanson et al. |
| 5,725,549 A | 3/1998 | Lam |
| 5,725,567 A | 3/1998 | Wolff et al. |
| 5,728,150 A | 3/1998 | McDonald et al. |
| 5,728,420 A | 3/1998 | Keogh |
| 5,731,326 A | 3/1998 | Hart et al. |
| 5,733,327 A | 3/1998 | Igaki et al. |
| 5,733,920 A | 3/1998 | Mansuri et al. |
| 5,733,925 A | 3/1998 | Kunz et al. |
| 5,735,897 A | 4/1998 | Buirge |
| 5,739,138 A | 4/1998 | Bianco et al. |
| 5,755,734 A | 5/1998 | Richter et al. |
| 5,755,772 A | 5/1998 | Evans et al. |
| 5,769,883 A | 6/1998 | Buscemi et al. |
| 5,776,184 A | 7/1998 | Tuch |
| 5,780,476 A | 7/1998 | Underiner et al. |
| 5,782,908 A | 7/1998 | Cahalan et al. |
| 5,788,979 A | 8/1998 | Alt et al. |
| 5,792,772 A | 8/1998 | Bianco et al. |
| 5,798,372 A | 8/1998 | Davies et al. |
| 5,799,384 A | 9/1998 | Schwartz et al. |
| 5,800,507 A | 9/1998 | Schwartz |
| 5,800,508 A | 9/1998 | Goicoechea et al. |
| 5,807,861 A | 9/1998 | Klein et al. |
| 5,811,447 A | 9/1998 | Kunz et al. |
| 5,820,917 A | 10/1998 | Tuch |
| 5,820,918 A | 10/1998 | Ronan et al. |
| 5,824,048 A | 10/1998 | Tuch |
| 5,824,049 A | 10/1998 | Ragheb et al. |
| 5,833,651 A | 11/1998 | Donovan et al. |
| 5,837,008 A | 11/1998 | Berg et al. |
| 5,837,313 A | 11/1998 | Ding et al. |
| 5,843,172 A | 12/1998 | Yan |
| 5,849,034 A | 12/1998 | Schwartz |
| 5,851,217 A | 12/1998 | Wolff et al. |
| 5,851,231 A | 12/1998 | Wolff et al. |
| 5,858,990 A | 1/1999 | Walsh |
| 5,861,027 A | 1/1999 | Trapp |
| 5,865,814 A | 2/1999 | Tuch |
| 5,871,535 A | 2/1999 | Wolff et al. |
| 5,873,904 A | 2/1999 | Ragheb et al. |
| 5,876,433 A | 3/1999 | Lunn |
| 5,879,697 A | 3/1999 | Ding et al. |
| 5,882,335 A | 3/1999 | Leone et al. |
| 5,891,108 A | 4/1999 | Leone et al. |
| 5,900,246 A | 5/1999 | Lambert |
| 5,902,266 A | 5/1999 | Leone et al. |
| 5,912,253 A * | 6/1999 | Cottens et al. ............... 514/291 |
| 5,932,580 A | 8/1999 | Levitzki et al. |
| 5,951,586 A | 9/1999 | Berg et al. |
| 5,957,971 A | 9/1999 | Schwartz |
| 5,972,027 A | 10/1999 | Johnson |
| 5,976,534 A | 11/1999 | Hart et al. |
| 5,977,163 A | 11/1999 | Li et al. |
| 5,980,553 A | 11/1999 | Gray et al. |
| 5,980,566 A | 11/1999 | Alt et al. |
| 5,980,972 A | 11/1999 | Ding |
| 5,981,568 A | 11/1999 | Kunz et al. |
| 5,985,307 A | 11/1999 | Hanson et al. |
| 5,997,468 A | 12/1999 | Wolff et al. |
| 6,004,346 A | 12/1999 | Wolff et al. |
| 6,039,721 A | 3/2000 | Johnson et al. |
| 6,059,813 A | 5/2000 | Vrba et al. |
| 6,071,305 A | 6/2000 | Brown et al. |
| 6,074,659 A | 6/2000 | Kunz et al. |
| 6,080,190 A | 6/2000 | Schwartz |
| 6,096,070 A | 8/2000 | Ragheb et al. |
| 6,120,536 A | 9/2000 | Dinge et al. |
| 6,136,798 A | 10/2000 | Cody et al. |
| 6,140,127 A | 10/2000 | Sprague |
| 6,146,358 A | 11/2000 | Rowe |
| 6,153,252 A | 11/2000 | Hossainy et al. |
| 6,171,232 B1 | 1/2001 | Papandreou et al. |
| 6,171,609 B1 | 1/2001 | Kunz |
| 6,177,272 B1 | 1/2001 | Nabel et al. |
| 6,214,901 B1 | 4/2001 | Chudzik et al. |
| 6,240,616 B1 | 6/2001 | Yan |
| 6,254,632 B1 | 7/2001 | Wu et al. |
| 6,258,121 B1 | 7/2001 | Yang et al. |
| 6,268,390 B1 | 7/2001 | Kunz |
| 6,273,913 B1 | 8/2001 | Wright et al. |
| 6,287,320 B1 | 9/2001 | Slepian |
| 6,287,628 B1 | 9/2001 | Hossainy et al. |
| 6,306,421 B1 | 10/2001 | Kunz et al. |
| 6,313,264 B1 | 11/2001 | Caggiano et al. |
| 6,369,039 B1 * | 4/2002 | Palasis et al. ............... 424/93.2 |
| 6,379,382 B1 | 4/2002 | Yang |
| 6,517,858 B1 | 2/2003 | Le Moal et al. |
| 6,585,764 B2 | 7/2003 | Wright et al. |
| 2001/0007083 A1 | 7/2001 | Roorda |
| 2002/0010418 A1 | 1/2002 | Lary et al. |
| 2002/0061326 A1 | 5/2002 | Li et al. |
| 2002/0082680 A1 | 6/2002 | Shanley |
| 2002/0082685 A1 | 6/2002 | Sirhan et al. |
| 2002/0095114 A1 | 7/2002 | Palasis |
| 2002/0103505 A1 | 8/2002 | Thompson |
| 2002/0103526 A1 | 8/2002 | Steinke |
| 2002/0119178 A1 | 8/2002 | Levesque et al. |
| 2002/0127327 A1 | 9/2002 | Schwarz et al. |
| 2002/0133224 A1 | 9/2002 | Bajgar et al. |
| 2002/0193475 A1 | 12/2002 | Hossainy et al. |

FOREIGN PATENT DOCUMENTS

| | | |
|---|---|---|
| EP | 604 022 A1 | 6/1994 |
| EP | 621 015 A1 | 10/1994 |
| EP | 623 354 A1 | 11/1994 |
| EP | 734698 A2 | 3/1996 |

| | | |
|---|---|---|
| EP | 0 712 615 | 5/1996 |
| EP | 716 836 A1 | 6/1996 |
| EP | 0 716 836 | 6/1996 |
| EP | 800801 A1 | 8/1996 |
| EP | 734 721 A1 | 10/1996 |
| EP | 0 761 251 | 3/1997 |
| EP | 830853 A1 | 7/1997 |
| EP | 0 850 651 | 7/1998 |
| EP | 0 938 878 A2 | 9/1999 |
| EP | 0 938 878 A3 | 9/1999 |
| EP | 950 386 A2 | 10/1999 |
| FR | 0 566 807 A1 | 4/1992 |
| GB | 0 662 307 A2 | 12/1951 |
| GB | 1 205 743 | 9/1970 |
| WO | WO 91/2779 | 9/1991 |
| WO | WO 92/15286 A1 | 9/1992 |
| WO | WO 94/01056 A1 | 1/1994 |
| WO | WO 94/21308 A1 | 9/1994 |
| WO | WO 94/21309 A1 | 9/1994 |
| WO | WO 94/24961 A1 | 11/1994 |
| WO | WO 96/00272 A1 | 1/1996 |
| WO | WO 96/26689 | 9/1996 |
| WO | WO 96/32907 | 10/1996 |
| WO | WO 96/34580 | 11/1996 |
| WO | WO 97/25000 | 7/1997 |
| WO | WO 97/33534 A1 | 9/1997 |
| WO | WO 98/13344 A1 | 4/1998 |
| WO | WO 98/19628 | 5/1998 |
| WO | WO 98/23228 | 6/1998 |
| WO | WO 98/23244 | 6/1998 |
| WO | WO 98/34669 | 8/1998 |
| WO | WO 98/36784 A1 | 8/1998 |
| WO | WO 98/47447 A1 | 10/1998 |
| WO | WO 98/56312 A1 | 12/1998 |
| WO | WO 00/21584 | 4/2000 |
| WO | WO 00/27445 A1 | 5/2000 |
| WO | WO 00/32255 A1 | 6/2000 |

* cited by examiner

ANTIINFLAMMATORY DRUG AND DELIVERY DEVICE

CROSS REFERENCE TO RELATED APPLICATIONS

This application is a continuation-in-part application of U.S. application Ser. No. 09/575,480, filed on May 19, 2000 which claims the benefit of U.S. Provisional Application No. 60/204,417, filed May 12, 2000 and claims the benefit of, U.S. Provisional Application No. 60/262,614, filed Jan. 18, 2001, U.S. Provisional Application No. 60/262,461, filed Jan. 18, 2001, U.S. Provisional Application No. 60/263,806, filed Jan. 24, 2001 and U.S. Provisional Application No. 60/263,979, filed Jan. 25, 2001.

BACKGROUND OF THE INVENTION

1. Field of the Invention

The present invention relates to drugs and drug delivery systems for the prevention and treatment of vascular disease, and more particularly to drugs and drug delivery systems for the prevention and treatment of neointimal hyperplasia.

2. Discussion of the Related Art

Many individuals suffer from circulatory disease caused by a progressive blockage of the blood vessels that perfuse the heart and other major organs with nutrients. More severe blockage of blood vessels in such individuals often leads to hypertension, ischemic injury, stroke, or myocardial infarction. Atherosclerotic lesions, which limit or obstruct coronary blood flow, are the major cause of ischemic heart disease. Percutaneous transluminal coronary angioplasty is a medical procedure whose purpose is to increase blood flow through an artery. Percutaneous transluminal coronary angioplasty is the predominant treatment for coronary vessel stenosis. The increasing use of this procedure is attributable to its relatively high success rate and its minimal invasiveness compared with coronary bypass surgery. A limitation associated with percutaneous transluminal coronary angioplasty is the abrupt closure of the vessel which may occur immediately after the procedure and restenosis which occurs gradually following the procedure. Additionally, restenosis is a chronic problem in patients who have undergone saphenous vein bypass grafting. The mechanism of acute occlusion appears to involve several factors and may result from vascular recoil with resultant closure of the artery and/or deposition of blood platelets and fibrin along the damaged length of the newly opened blood vessel.

Restenosis after percutaneous transluminal coronary angioplasty is a more gradual process initiated by vascular injury. Multiple processes, including thrombosis, inflammation, growth factor and cytokine release, cell proliferation, cell migration and extracellular matrix synthesis each contribute to the restenotic process.

While the exact mechanism of restenosis is not completely understood, the general aspects of the restenosis process have been identified. In the normal arterial wall, smooth muscle cells proliferate at a low rate, approximately less than 0.1 percent per day. Smooth muscle cells in the vessel walls exist in a contractile phenotype characterized by eighty to ninety percent of the cell cytoplasmic volume occupied with the contractile apparatus. Endoplasmic reticulum, Golgi, and free ribosomes are few and are located in the perinuclear region. Extracellular matrix surrounds the smooth muscle cells and is rich in heparin-like glycosylaminoglycans which are believed to be responsible for maintaining smooth muscle cells in the contractile phenotypic state (Campbell and Campbell, 1985).

Upon pressure expansion of an intracoronary balloon catheter during angioplasty, smooth muscle cells within the vessel wall become injured, initiating a thrombotic and inflammatory response. Cell derived growth factors such as platelet derived growth factor, fibroblast growth factor, epidermal growth factor, thrombin, etc., released from platelets, invading macrophages and/or leukocytes, or directly from the smooth muscle cells provoke proliferative and migratory responses in medial smooth muscle cells. These cells undergo a change from the contractile phenotype to a synthetic phenotype characterized by only a few contractile filament bundles, extensive rough endoplasmic reticulum, Golgi and free ribosomes. Proliferation/migration usually begins within one to two days post-injury and peaks several days thereafter (Campbell and Campbell, 1987; Clowes and Schwartz, 1985).

Daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells invade the site of vascular injury. Within three to seven days post-injury, inflammatory cells have migrated to the deeper layers of the vessel wall. In animal models employing either balloon injury or stent implantation, inflammatory cells may persist at the site of vascular injury for at least thirty days (Tanaka et al., 1993; Edelman et al., 1998). Inflammatory cells therefore are present and may contribute to both the acute and chronic phases of restenosis.

Numerous agents have been examined for presumed anti-proliferative actions in restenosis and have shown some activity in experimental animal models. Some of the agents which have been shown to successfully reduce the extent of intimal hyperplasia in animal models include: heparin and heparin fragments (Clowes, A. W. and Karnovsky M., Nature 265: 25–26, 1977; Guyton, J. R. et al., Circ. Res., 46: 625–634, 1980; Clowes, A. W. and Clowes, M. M., Lab. Invest. 52: 611–616, 1985; Clowes, A. W. and Clowes, M. M., Circ. Res. 58: 839–845, 1986; Majesky et al., Circ. Res. 61: 296–300, 1987; Snow et al., Am. J. Pathol. 137: 313–330, 1990; Okada, T. et al., Neurosurgery 25: 92–98, 1989), colchicine (Currier, J. W. et al., Circ. 80: 11–66, 1989), taxol (Sollot, S. J. et al., J. Clin. Invest. 95: 1869–1876, 1995), angiotensin converting enzyme (ACE) inhibitors (Powell, J. S. et al., Science, 245: 186–188, 1989), angiopeptin (Lundergan, C. F. et al. Am. J. Cardiol. 17(Suppl. B):132B-136B, 1991), cyclosporin A (Jonasson, L. et al., Proc. Natl., Acad. Sci., 85: 2303, 1988), goat-anti-rabbit PDGF antibody (Ferns, G. A. A., et al., Science 253: 1129–1132, 1991), terbinafine (Nemecek, G. M. et al., J. Pharmacol. Exp. Thera. 248: 1167–1174, 1989), trapidil (Liu, M. W. et al., Circ. 81: 1089–1093, 1990), tranilast (Fukuyama, J. et al., Eur. J. Pharmacol. 318: 327–332, 1996), interferon-gamma (Hansson, G. K. and Holm, J., Circ. 84:1266–1272, 1991), rapamycin (Marx, S. O. et al., Circ. Res. 76: 412417, 1995), corticosteroids (Colburn, M. D. et al., J. Vasc. Surg. 15: 510–518, 1992), see also Berk, B. C. et al., J. Am. Coll. Cardiol. 17: 111 B-117B, 1991), ionizing radiation (Weinberger, J. et al., Int. J. Rad. Onc. Biol. Phys. 36: 767–775, 1996), fusion toxins (Farb, A. et al., Circ. Res. 80: 542–550, 1997) antisense oligonucleotides (Simons, M. et al., Nature 359: 67–70, 1992) and gene vectors (Chang, M. W. et al., J. Clin. Invest. 96: 2260–2268, 1995). Anti-proliferative effects on smooth muscle cells in vitro have been demonstrated for many of these agents, including heparin and heparin conjugates, taxol, tranilast, colchicine, ACE inhibitors, fusion toxins, antisense oligonucleotides, rapamycin and ionizing radiation. Thus, agents with diverse mechanisms of smooth muscle cell inhibition may have therapeutic utility in reducing intimal hyperplasia.

However, in contrast to animal models, attempts in human angioplasty patients to prevent restenosis by systemic pharmacologic means have thus far been unsuccessful. Neither aspirin-dipyridamole, ticlopidine, anti-coagulant therapy (acute heparin, chronic warfarin, hirudin or hirulog), thromboxane receptor antagonism nor steroids have been effective in preventing restenosis, although platelet inhibitors have been effective in preventing acute reocclusion after angioplasty (Mak and Topol, 1997; Lang et al., 1991; Popma et al., 1991). The platelet GP IIb/IIIa receptor, antagonist, Reopro is still under study but has not shown promising results for the reduction in restenosis following angioplasty and stenting. Other agents, which have also been unsuccessful in the prevention of restenosis, include the calcium channel antagonists, prostacyclin mimetics, angiotensin converting enzyme inhibitors, serotonin receptor antagonists, and anti-proliferative agents. These agents must be given systemically, however, and attainment of a therapeutically effective dose may not be possible; anti-proliferative (or anti-restenosis) concentrations may exceed the known toxic concentrations of these agents so that levels sufficient to produce smooth muscle inhibition may not be reached (Mak and Topol, 1997; Lang et al., 1991; Popma et al., 1991).

Additional clinical trials in which the effectiveness for preventing restenosis utilizing dietary fish oil supplements or cholesterol lowering agents has been examined showing either conflicting or negative results so that no pharmacological agents are as yet clinically available to prevent post-angioplasty restenosis (Mak and Topol, 1997; Franklin and Faxon, 1993: Serruys, P. W. et al., 1993). Recent observations suggest that the antilipid/antioxidant agent, probucol may be useful in preventing restenosis but this work requires confirmation (Tardif et al., 1997; Yokoi, et al., 1997). Probucol is presently not approved for use in the United States and a thirty-day pretreatment period would preclude its use in emergency angioplasty. Additionally, the application of ionizing radiation has shown significant promise in reducing or preventing restenosis after angioplasty in patients with stents (Teirstein et al., 1997). Currently, however, the most effective treatments for restenosis are repeat angioplasty, atherectomy or coronary artery bypass grafting, because no therapeutic agents currently have Food and Drug Administration approval for use for the prevention of post-angioplasty restenosis.

Unlike systemic pharmacologic therapy, stents have proven effective in significantly reducing restenosis. Typically, stents are balloon-expandable slotted metal tubes (usually, but not limited to, stainless steel), which, when expanded within the lumen of an angioplastied coronary artery, provide structural support through rigid scaffolding to the arterial wall. This support is helpful in maintaining vessel lumen patency. In two randomized clinical trials, stents increased angiographic success after percutaneous transluminal coronary angioplasty, by increasing minimal lumen diameter and reducing, but not eliminating, the incidence of restenosis at six months (Serruys et al., 1994; Fischman et al., 1994).

Additionally, the heparin coating of stents appears to have the added benefit of producing a reduction in sub-acute thrombosis after stent implantation (Serruys et al., 1996). Thus, sustained mechanical expansion of a stenosed coronary artery with a stent has been shown to provide some measure of restenosis prevention, and the coating of stents with heparin has demonstrated both the feasibility and the clinical usefulness of delivering drugs locally, at the site of injured tissue.

Accordingly, there exists a need for effective drugs and drug delivery systems for the effective prevention and treatment of neointimal thickening that occurs after percutaneous transluminal coronary angioplasty and stent implantation.

SUMMARY OF THE INVENTION

The drugs and drug delivery systems of the present invention provide a means for overcoming the difficulties associated with the methods and devices currently in use as briefly described above.

In accordance with one aspect, the present invention is directed to a method for the treatment of intimal hyperplasia in vessel walls. The method comprises the controlled delivery, by release from an intraluminal medical device, of an anti-inflammatory agent in therapeutic dosage amounts.

In accordance with another aspect, the present invention is directed to a drug delivery device. The drug delivery device comprises an intraluminal medical device and a therapeutic dosage of an agent releasably affixed to the intraluminal medical device for the treatment of inflammation caused by injury.

In accordance with another aspect, the present invention is directed to a method for the treatment of inflammation in vessel walls. The method comprises the controlled delivery, by release from an intraluminal medical device, of an anti-inflammatory agent in therapeutic dosage amounts.

The drugs and drug delivery systems of the present invention utilize a stent or graft in combination with rapamycin or other drugs/agents/compounds to prevent and treat neointimal hyperplasia, i.e. restenosis, following percutaneous transluminal coronary angioplasty and stent implantation. It has been determined that rapamycin functions to inhibit smooth muscle cell proliferation through a number of mechanisms. It has also been determined that rapamycin eluting stent coatings produce superior effects in humans, when compared to animals, with respect to the magnitude and duration of the reduction in neointimal hyperplasia. Rapamycin administration from a local delivery platform also produces an anti-inflammatory effect in the vessel wall that is distinct from and complimentary to its smooth muscle cell anti-proliferative effect. In addition, it has also been demonstrated that rapamycin inhibits constrictive vascular remodeling in humans.

Other drugs, agents or compounds which mimic certain actions of rapamycin may also be utilized in combination with local delivery systems or platforms.

The local administration of drugs, agents or compounds to stented vessels have the additional therapeutic benefit of higher tissue concentration than that which would be achievable through the systemic administration of the same drugs, agents or compounds. Other benefits include reduced systemic toxicity, single treatment, and ease of administration. An additional benefit of a local delivery device and drug, agent or compound therapy may be to reduce the dose of the therapeutic drugs, agents or compounds and thus limit their toxicity, while still achieving a reduction in restenosis.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
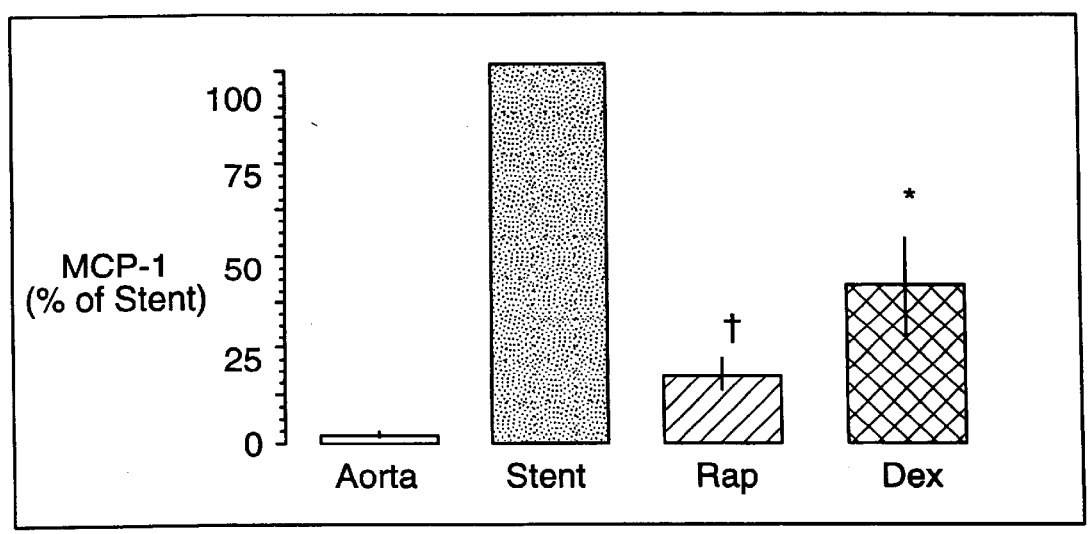
FIG. 1 is a chart indicating the effectiveness of rapamycin as an anti-inflammatory relative to other anti-inflammatories.

As stated above, the proliferation of vascular smooth muscle cells in response to mitogenic stimuli that are released during balloon angioplasty and stent implantation is the primary cause of neointimal hyperplasia. Excessive neointimal hyperplasia can often lead to impairment of blood flow, cardiac ischemia and the need for a repeat intervention in selected patients in high risk treatment groups. Yet repeat revascularization incurs risk of patient morbidity and mortality while adding significantly to the cost of health care. Given the widespread use of stents in interventional practice, there is a clear need for safe and effective inhibitors of neointimal hyperplasia.

Rapamycin is a macroyclic triene antibiotic produced by streptomyces hygroscopicus as disclosed in U.S. Pat. No. 3,929,992. It has been found that rapamycin inhibits the proliferation of vascular smooth muscle cells in vivo. Accordingly, rapamycin may be utilized in treating intimal smooth muscle cell hyperplasia, restenosis and vascular occlusion in a mammal, particularly following either biologically or mechanically mediated vascular injury, or under conditions that would predispose a mammal to suffering such a vascular injury. Rapamycin functions to inhibit smooth muscle cell proliferation and does not interfere with the re-endothelialization of the vessel walls.

Rapamycin functions to inhibit smooth muscle cell proliferation through a number of mechanisms. In addition, rapamycin reduces the other effects caused by vascular injury, for example, inflammation. The operation and various functions of rapamycin are described in detail below. Rapamycin as used throughout this application shall include rapamycin, rapamycin analogs, derivatives and congeners that bind FKBP12 and possess the same pharmacologic properties as rapamycin.

Rapamycin reduces vascular hyperplasia by antagonizing smooth muscle proliferation in response to mitogenic signals that are released during angioplasty. Inhibition of growth factor and cytokine mediated smooth muscle proliferation at the late G1 phase of the cell cycle is believed to be the dominant mechanism of action of rapamycin. However, rapamycin is also known to prevent T-cell proliferation and differentiation when administered systemically. This is the basis for its immunosuppresive activity and its ability to prevent graft rejection.

The molecular events that are responsible for the actions of rapamycin, a known anti-proliferative, which acts to reduce the magnitude and duration of neointimal hyperplasia, are still being elucidated. It is known, however, that rapamycin enters cells and binds to a high-affinity cytosolic protein called FKBP12. The complex of rapamycin and FKPB12 in turn binds to and inhibits a phosphoinositide (PI)-3 kinase called the "mammalian Target of Rapamycin" or TOR. TOR is a protein kinase that plays a key role in mediating the downstream signaling events associated with mitogenic growth factors and cytokines in smooth muscle cells and T lymphocytes. These events include phosphorylation of p27, phosphorylation of p70 s6 kinase and phosphorylation of 4BP-1, an important regulator of protein translation.

It is recognized that rapamycin reduces restenosis by inhibiting neointimal hyperplasia. However, there is evidence that rapamycin may also inhibit the other major component of restenosis, namely, negative remodeling. Remodeling is a process whose mechanism is not clearly understood but which results in shrinkage of the external elastic lamina and reduction in lumenal area over time, generally a period of approximately three to six months in humans.

Negative or constrictive vascular remodeling may be quantified angiographically as the percent diameter stenosis at the lesion site where there is no stent to obstruct the process. If late lumen loss is abolished in-lesion, it may be inferred that negative remodeling has been inhibited. Another method of determining the degree of remodeling involves measuring in-lesion external elastic lamina area using intravascular ultrasound (IVUS). Intravascular ultrasound is a technique that can image the external elastic lamina as well as the vascular lumen. Changes in the external elastic lamina proximal and distal to the stent from the post-procedural timepoint to four-month and twelve-month follow-ups are reflective of remodeling changes.

Evidence that rapamycin exerts an effect on remodeling comes from human implant studies with rapamycin coated stents showing a very low degree of restenosis in-lesion as well as in-stent. In-lesion parameters are usually measured approximately five millimeters on either side of the stent i.e. proximal and distal. Since the stent is not present to control remodeling in these zones which are still affected by balloon expansion, it may be inferred that rapamycin is preventing vascular remodeling.

The data in Table 1 below illustrate that in-lesion percent diameter stenosis remains low in the rapamycin treated groups, even at twelve months. Accordingly, these results support the hypothesis that rapamycin reduces remodeling.

TABLE 1.0

| Angiographic In-Lesion Percent Diameter Stenosis (%, mean ± SD and "n=" In Patients Who Received a Rapamycin-Coated Stent | | | |
|---|---|---|---|
| Coating Group | Post Placement | 4–6 month Follow Up | 12 month Follow Up |
| Brazil | 10.6 ± 5.7 (30) | 13.6 ± 8.6 (30) | 22.3 ± 7.2 (15) |
| Netherlands | 14.7 ± 8.8 | 22.4 ± 6.4 | — |

Additional evidence supporting a reduction in negative remodeling with rapamycin comes from intravascular ultrasound data that was obtained from a first-in-man clinical program as illustrated in Table 2 below.

TABLE 2.0

Matched IVUS data in Patients Who Received a Rapamycin-Coated Stent

| IVUS Parameter | Post (n=) | 4-Month Follow-Up (n=) | 12-Month Follow-Up (n=) |
|---|---|---|---|
| Mean proximal vessel area (mm$^2$) | 16.53 ± 3.53 (27) | 16.31 ± 4.36 (28) | 13.96 ± 2.26 (13) |
| Mean distal vessel area (mm$^2$) | 13.12 ± 3.68 (26) | 13.53 ± 4.17 (26) | 12.49 ± 3.25 (14) |

The data illustrated that there is minimal loss of vessel area proximally or distally which indicates that inhibition of negative remodeling has occurred in vessels treated with rapamycin-coated stents.

Other than the stent itself, there have been no effective solutions to the problem of vascular remodeling. Accordingly, rapamycin may represent a biological approach to controlling the vascular remodeling phenomenon.

It may be hypothesized that rapamycin acts to reduce negative remodeling in several ways. By specifically blocking the proliferation of fibroblasts in the vascular wall in response to injury, rapamycin may reduce the formation of vascular scar tissue. Rapamycin may also affect the translation of key proteins involved in collagen formation or metabolism.

Rapamycin used in this context includes rapamycin and all analogs, derivatives and congeners that bind FKBP12 and possess the same pharmacologic properties as rapamycin.

In a preferred embodiment, the rapamycin is delivered by a local delivery device to control negative remodeling of an arterial segment after balloon angioplasty as a means of reducing or preventing restenosis. While any delivery device may be utilized, it is preferred that the delivery device comprises a stent that includes a coating or sheath which elutes or releases rapamycin. The delivery system for such a device may comprise a local infusion catheter that delivers rapamycin at a rate controlled by the administrator.

Rapamycin may also be delivered systemically using an oral dosage form or a chronic injectable depot form or a patch to deliver rapamycin for a period ranging from about seven to forty-five days to achieve vascular tissue levels that are sufficient to inhibit negative remodeling. Such treatment is to be used to reduce or prevent restenosis when administered several days prior to elective angioplasty with or without a stent.

Data generated in porcine and rabbit models show that the release of rapamycin into the vascular wall from a nonerodible polymeric stent coating in a range of doses (35–430 ug/15–18 mm coronary stent) produces a peak fifty to fifty-five percent reduction in neointimal hyperplasia as set forth in Table 3 below. This reduction, which is maximal at about twenty-eight to thirty days, is typically not sustained in the range of ninety to one hundred eighty days in the porcine model as set forth in Table 4 below.

TABLE 3.0

Animal Studies with Rapamycin-coated stents.
Values are mean ± Standard Error of Mean

| Study | Duration | Stent[1] | Rapamycin | N | Neointimal Area (mm$^2$) | % Change From Polyme | % Change From Metal |
|---|---|---|---|---|---|---|---|
| Porcine | | | | | | | |
| 98009 | 14 days | Metal | | 8 | 2.04 ± 0 17 | | |
| | | 1X + rapamycin | 153 μg | 8 | 1.66 ± 0.17* | −42% | −19% |
| | | 1X + TC300 + rapamycin | 155 μg | 8 | 1.51 ± 0.19* | −47% | −26% |
| 99005 | 28 days | Metal | | 10 | 2.29 ± 0.21 | | |
| | | | | 9 | 3.91 ± 0.60** | | |
| | | 1X + TC30 + rapamycin | 130 μg | 8 | 2.81 ± 0.34 | | +23% |
| | | 1X + TC100 + rapamycin | 120 μg | 9 | 2.62 ± 0.21 | | +14% |
| 99006 | 28 days | Metal | | 12 | 4.57 ± 0.46 | | |
| | | EVA/BMA 3X | | 12 | 5.02 ± 0.62 | | +10% |
| | | 1X + rapamycin | 125 μg | 11 | 2.84 ± 0.31* ** | −43% | −38% |
| | | 3X + rapamycin | 430 μg | 12 | 3.06 ± 0.17* ** | −39% | −33% |
| | | 3X + rapamycin | 157 μg | 12 | 2.77 ± 0.41* ** | −45% | −39% |
| 99011 | 28 days | Metal | | 11 | 3.09 ± 0.27 | | |
| | | | | 11 | 4.52 ± 0.37 | | |
| | | 1X + rapamycin | 189 μg | 14 | 3.05 ± 0.35 | | −1% |
| | | 3X + rapamycin/dex | 182/363 μg | 14 | 2.72 ± 0.71 | | −12% |
| 99021 | 60 days | Metal | | 12 | 2.14 ± 0.25 | | |
| | | 1X + rapamycin | 181 μg | 12 | 2.95 ± 0.38 | | +38% |
| 99034 | 28 days | Metal | | 8 | 5.24 ± 0.58 | | |
| | | 1X + rapamycin | 186 μg | 8 | 2.47 ± 0.33** | | −53% |
| | | 3X + rapamycin/dex | 185/369 μg | 6 | 2.42 ± 0.64** | | −54% |
| 20001 | 28 days | Metal | | 6 | 1.81 ± 0.09 | | |
| | | 1X + rapamycin | 172 μg | 5 | 1.66 ± 0.44 | | −8% |
| 20007 | 30 days | Metal | | 9 | 2.94 ± 0.43 | | |
| | | 1XTC + rapamycin | 155 μg | 10 | 1.40 ± 0.11* | | −52%* |

TABLE 3.0-continued

Animal Studies with Rapamycin-coated stents.
Values are mean ± Standard Error of Mean

| Study | Duration | Stent[1] | Rapamycin | N | Neointimal Area (mm$^2$) | % Change From Polyme | % Change From Metal |
|---|---|---|---|---|---|---|---|
| Rabbit | | | | | | | |
| 99019 | 28 days | Metal | | 8 | 1.20 ± 0.07 | | |
| | | EVA/BMA 1X | | 10 | 1.26 ± 0.16 | | +5% |
| | | 1X + rapamycin | 64 μg | 9 | 0.92 ± 0.14 | −27% | −23% |
| | | 1X + rapamycin | 196 μg | 10 | 0.66 ± 0.12* ** | −48% | −45% |
| 99020 | 28 days | Metal | | 12 | 1.18 ± 0.10 | | |
| | | EVA/BMA 1X + rapamycin | 197 μg | 8 | 0.81 ± 0.16 | | −32% |

[1]Stent nomenclature: EVA/BMA 1X, 2X, and 3X signifies approx. 500 μg, 1000 μg, and 1500 μg total mass (polymer + drug), respectively.
TC, top coat of 30 μg, 100 μg, or 300 μg drug-free BMA;
Biphasic; 2x 1X layers of rapamycin in EVA/BMA spearated by a 100 μg drug-free BMA layer.
[2]0.25 mg/kg/d × 14 d preceeded by a loading dose of 0.5 mg/kg/d × 3d prior to stent implantation.
*p < 0 05 from EVA/BMA control.
**p < 0.05 from Metal;
Inflammation score: (0 = essentially no intimal involvement;
1 = <25% intima involved;
2 = ≧25% intima involved;
3 = >50% intima involved).

TABLE 4.0

180 day Porcine Study with Rapamycin-coated stents.
Values are mean ± Standard Error of Mean

| Study | Duration | Stent[1] | Rapamycin | N | Neointimal Area (mm$^2$) | % Change From Polyme | % Change From Metal | Inflammation Score # |
|---|---|---|---|---|---|---|---|---|
| 20007 | 3 days | Metal | | 10 | 0.38 ± 0.06 | | | 1.05 ± 0.06 |
| (ETP-2-002233-P) | | 1XTC + rapamycin | 155 μg | 10 | 0.29 ± 0 03 | | −24% | 1.08 ± 0.04 |
| | 30 days | Metal | | 9 | 2.94 ± 0.43 | | | 0.11 ± 0.08 |
| | | 1XTC + rapamycin | 155 μg | 10 | 1.40 ± 0.11* | | −52%* | 0.25 ± 0.10 |
| | 90 days | Metal | | 10 | 3.45 ± 0.34 | | | 0.20 ± 0.08 |
| | | 1XTC + rapamycin | 155 μg | 10 | 3.03 ± 0.29 | | −12% | 0.80 ± 0.23 |
| | | 1X + rapamycin | 171 μg | 10 | 2.86 ± 0.35 | | −17% | 0.60 ± 0.23 |
| | 180 days | Metal | | 10 | 3.65 ± 0.39 | | | 0.65 ± 0.21 |
| | | 1XTC + rapamycin | 155 μg | 10 | 3.34 ± 0.31 | | −8% | 1.50 ± 0.34 |
| | | 1X + rapamycin | 171 μg | 10 | 3.87 ± 0.28 | | +6% | 1.68 ± 0.37 |

The release of rapamycin into the vascular wall of a human from a nonerodible polymeric stent coating provides superior results with respect to the magnitude and duration of the reduction in neointimal hyperplasia within the stent as compared to the vascular walls of animals as set forth above.

Humans implanted with a rapamycin coated stent comprising rapamycin in the same dose range as studied in animal models using the same polymeric matrix, as described above, reveal a much more profound reduction in neointimal hyperplasia than observed in animal models, based on the magnitude and duration of reduction in neointima. The human clinical response to rapamycin reveals essentially total abolition of neointimal hyperplasia inside the stent using both angiographic and intravascular ultrasound measurements. These results are sustained for at least one year as set forth in Table 5 below.

TABLE 5.0

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Procedure Success (QCA) | 100.0% (45/45) | [92.1%, 100.0%] |
| 4-month In-Stent Diameter Stenosis (%) | | |
| Mean ± SD (N) | 4.8% ± 6.1% (30) | [2.6%, 7.0%] |
| Range (min, max) | (−8.2%, 14.9%) | |
| 6-month In-Stent Diameter Stenosis (%) | | |
| Mean ± SD (N) | 8.9% ± 7.6% (13) | [4.8%, 13.0%] |
| Range (min, max) | (−2.9%, 20.4%) | |
| 12-month In-Stent | | |

TABLE 5.0-continued

Patients Treated (N = 45 patients) with a Rapamycin-coated Stent

| Effectiveness Measures | Sirolimus FIM (N = 45 Patients, 45 Lesions) | 95% Confidence Limit |
|---|---|---|
| Diameter Stenosis (%) | | |
| Mean ± SD (N) | 8.9% ± 6.1% (15) | [5.8%, 12.0%] |
| Range (min, max) | (−3.0%, 22.0%) | |
| 4-month In-Stent Late Loss (mm) | | |
| Mean ± SD (N) | 0.00 ± 0.29 (30) | [−0.10, 0.10] |
| Range (min, max) | (−0.51, 0.45) | |
| 6-month In-Stent Late Loss (mm) | | |
| Mean ± SD (N) | 0.25 ± 0.27 (13) | [0.10, 0.39] |
| Range (min, max) | (−0.51, 0.91) | |
| 12-month In-Stent Late Loss (mm) | | |
| Mean ± SD (N) | 0.11 ± 0.36 (15) | [−0.08, 0.29] |
| Range (min, max) | (−0.51, 0.82) | |
| 4-month Obstruction Volume (%) (IVUS) | | |
| Mean ± SD (N) | 10.48% ± 2.78% (28) | [9.45%, 11.51%] |
| Range (min, max) | (4.60%, 16.35%) | |
| 6-month Obstruction Volume (%) (IVUS) | | |
| Mean ± SD (N) | 7.22% ± 4.60% (13) | [4.72%, 9.72%], |
| Range (min, max) | (3.82%, 19.88%) | |
| 12-month Obstruction Volume (%) (IVUS) | | |
| Mean ± SD (N) | 2.11% ± 5.28% (15) | [0.00%, 4.78%], |
| Range (min, max) | (0.00%, 19.89%) | |
| 6-month Target Lesion Revascularization (TLR) | 0.0% (0/30) | [0.0%, 9.5%] |
| 12-month Target Lesion Revascularization (TLR) | 0.0% (0/15) | [0.0%, 18.1%] |

QCA = Quantitative Coronary Angiography
SD = Standard Deviation
IVUS = Intravascular Ultrasound Rapamycin produces an unexpected benefit in humans when delivered from a stent by causing a profound reduction in in-stent neointimal hyperplasia that is sustained for at least one year. The magnitude and duration of this benefit in humans is not predicted from animal model data. Rapamycin used in this context includes rapamycin and all analogs, derivatives and congeners that bind FKBP12 and possess the same pharmacologic properties as rapamycin.

These results may be due to a number of factors. For example, the greater effectiveness of rapamycin in humans is due to greater sensitivity of its mechanism(s) of action toward the pathophysiology of human vascular lesions compared to the pathophysiology of animal models of angioplasty. In addition, the combination of the dose applied to the stent and the polymer coating that controls the release of the drug is important in the effectiveness of the drug.

As stated above, rapamycin reduces vascular hyperplasia by antagonizing smooth muscle proliferation in response to mitogenic signals that are released during angioplasty injury. Also, it is known that rapamycin prevents T-cell proliferation and differentiation when administered systemically. It has also been determined that rapamycin exerts a local inflammatory effect in the vessel wall when administered from a stent in low doses for a sustained period of time (approximately two to six weeks). The local anti-inflammatory benefit is profound and unexpected. In combination with the smooth muscle anti-proliferative effect, this dual mode of action of rapamycin may be responsible for its exceptional efficacy.

Accordingly, rapamycin delivered from a local device platform, reduces neointimal hyperplasia by a combination of anti-inflammatory and smooth muscle anti-proliferative effects. Rapamycin used in this context means rapamycin and all analogs, derivatives and congeners that bind FKBP12 and possess the same pharmacologic properties as rapamycin. Local device platforms include stent coatings, stent sheaths, grafts and local drug infusion catheters or porous balloons or any other suitable means for the in situ or local delivery of drugs, agents or compounds.

The anti-inflammatory effect of rapamycin is evident in data from an experiment, illustrated in Table 6, in which rapamycin delivered from a stent was compared with dexamethasone delivered from a stent. Dexamethasone, a potent steroidal anti-inflammatory agent, was used as a reference standard. Although dexamethasone is able to reduce inflammation scores, rapamycin is far more effective than dexamethasone in reducing inflammation scores. In addition, rapamycin significantly reduces neointimal hyperplasia, unlike dexamethasone.

TABLE 6.0

| Group Rapamycin Rap | N= | Neointimal Area (mm$^2$) | % Area Stenosis | Inflammation Score |
|---|---|---|---|---|
| Uncoated | 8 | 5.24 ± 1.65 | 54 ± 19 | 0.97 ± 1.00 |
| Dexamethasone (Dex) | 8 | 4.31 ± 3.02 | 45 ± 31 | 0.39 ± 0.24 |
| Rapamycin | 7 | 2.47 ± 0.94* | 26 ± 10* | 0.13 ± 0.19* |
| Rap + Dex | 6 | 2.42 ± 1.58* | 26 ± 18* | 0.17 ± 0.30* |

*significance level P < 0.05

Rapamycin has also been found to reduce cytokine levels in vascular tissue when delivered from a stent. The data in FIG. 1 illustrates that rapamycin is highly effective in reducing monocyte chemotactic protein (MCP-1) levels in the vascular wall. MCP-1 is an example of a proinflammatory/chemotactic cytokine that is elaborated during vessel injury. Reduction in MCP-1 illustrates the beneficial effect of rapamycin in reducing the expression of proinflammatory mediators and contributing to the anti-inflammatory effect of rapamycin delivered locally from a stent. It is recognized that vascular inflammation in response to injury is a major contributor to the development of neointimal hyperplasia.

Since rapamycin may be shown to inhibit local inflammatory events in the vessel it is believed that this could explain the unexpected superiority of rapamycin in inhibiting neointima.

As set forth above, rapamycin functions on a number of levels to produce such desired effects as the prevention of T-cell proliferation, the inhibition of negative remodeling, the reduction of inflammation, and the prevention of smooth muscle cell proliferation. While the exact mechanisms of these functions are not completely known, the mechanisms that have been identified may be expanded upon.

Studies with rapamycin suggest that the prevention of smooth muscle cell proliferation by blockade of the cell cycle is a valid strategy for reducing neointimal hyperplasia. Dramatic and sustained reductions in late lumen loss and neointimal plaque volume have been observed in patients receiving rapamycin delivered locally from a stent. The present invention expands upon the mechanism of rapamycin to include additional approaches to inhibit the cell cycle and reduce neointimal hyperplasia without producing toxicity.

The cell cycle is a tightly controlled biochemical cascade of events that regulate the process of cell replication. When cells are stimulated by appropriate growth factors, they move from $G_0$ (quiescence) to the G1 phase of the cell cycle. Selective inhibition of the cell cycle in the G1 phase, prior to DNA replication (S phase), may offer therapeutic advantages of cell preservation and viability while retaining anti-proliferative efficacy when compared to therapeutics that act later in the cell cycle i.e. at S, G2 or M phase.

Accordingly, the prevention of intimal hyperplasia in blood vessels and other conduit vessels in the body may be achieved using cell cycle inhibitors that act selectively at the G1 phase of the cell cycle. These inhibitors of the G1 phase of the cell cycle may be small molecules, peptides, proteins, oligonucleotides or DNA sequences. More specifically, these drugs or agents include inhibitors of cyclin dependent kinases (cdk's) involved with the progression of the cell cycle through the G1 phase, in particular cdk2 and cdk4.

Examples of drugs, agents or compounds that act selectively at the G1 phase of the cell cycle include small molecules such as flavopiridol and its structural analogs that have been found to inhibit cell cycle in the late G1 phase by antagonism of cyclin dependent kinases. Therapeutic agents that elevate an endogenous kinase inhibitory protein$^{kip}$ called P27, sometimes referred to as P27$^{kip1}$, that selectively inhibits cyclin dependent kinases may be utilized. This includes small molecules, peptides and proteins that either block the degradation of P27 or enhance the cellular production of P27, including gene vectors that can transfact the gene to produce P27. Staurosporin and related small molecules that block the cell cycle by inhibiting protein kinases may be utilized. Protein kinase inhibitors, including the class of tyrphostins that selectively inhibit protein kinases to antagonize signal transduction in smooth muscle in response to a broad range of growth factors such as PDGF and FGF may also be utilized.

Any of the drugs, agents or compounds discussed above may be administered either systemically, for example, orally, intravenously, intramuscularly, subcutaneously, nasally or intradermally, or locally, for example, stent coating, stent covering or local delivery catheter. In addition, the drugs or agents discussed above may be formulated for fast-release or slow release with the objective of maintaining the drugs or agents in contact with target tissues for a period ranging from three days to eight weeks.

As set forth above, the complex of rapamycin and FKPB12 binds to and inhibits a phosphoinositide (PI)-3 kinase called the mammalian Target of Rapamycin or TOR. An antagonist of the catalytic activity of TOR, functioning as either an active site inhibitor or as an allosteric modulator, i.e. an indirect inhibitor that allosterically modulates, would mimic the actions of rapamycin but bypass the requirement for FKBP12. The potential advantages of a direct inhibitor of TOR include better tissue penetration and better physical/chemical stability. In addition, other potential advantages include greater selectivity and specificity of action due to the specificity of an antagonist for one of multiple isoforms of TOR that may exist in different tissues, and a potentially different spectrum of downstream effects leading to greater drug efficacy and/or safety.

The inhibitor may be a small organic molecule (approximate mw<1000), which is either a synthetic or naturally derived product. Wortmanin may be an agent which inhibits the function of this class of proteins. It may also be a peptide or an oligonucleotide sequence. The inhibitor may be administered either sytemically (orally, intravenously, intramuscularly, subcutaneously, nasally, or intradermally) or locally (stent coating, stent covering, local drug delivery catheter). For example, the inhibitor may be released into the vascular wall of a human from a nonerodible polymeric stent coating. In addition, the inhibitor may be formulated for fast-release or slow release with the objective of maintaining the rapamycin or other drug, agent or compound in contact with target tissues for a period ranging from three days to eight weeks.

As stated previously, the implantation of a coronary stent in conjunction with balloon angioplasty is highly effective in treating acute vessel closure and may reduce the risk of restenosis. Intravascular ultrasound studies (Mintz et al., 1996) suggest that coronary stenting effectively prevents vessel constriction and that most of the late luminal loss after stent implantation is due to plaque growth, probably related to neointimal hyperplasia. The late luminal loss after coronary stenting is almost two times higher than that observed after conventional balloon angioplasty. Thus, inasmuch as stents prevent at least a portion of the restenosis process, the use of drugs, agents or compounds which prevent inflammation and proliferation, or prevent proliferation by multiple mechanisms, combined with a stent may provide the most efficacious treatment for post-angioplasty restenosis.

The local delivery of drugs, agents or compounds from a stent has the following advantages; namely, the prevention of vessel recoil and remodeling through the scaffolding action of the stent and the drugs, agents or compounds and the prevention of multiple components of neointimal hyperplasia. This local administration of drugs, agents or compounds to stented coronary arteries may also have additional therapeutic benefit. For example, higher tissue concentrations would be achievable than that which would occur with systemic administration, reduced systemic toxicity, and single treatment and ease of administration. An additional benefit of drug therapy may be to reduce the dose of the therapeutic compounds, thereby limiting their toxicity, while still achieving a reduction in restenosis.

There are a multiplicity of different stents that may be utilized following percutaneous transluminal coronary angioplasty. Although any number of stents may be utilized in accordance with the present invention, for simplicity, one particular stent will be described in exemplary embodiments of the present invention. The skilled artisan will recognize that any number of stents may be utilized in connection with the present invention.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. As set forth below, self-expanding stents may also be utilized.

Figure 2:
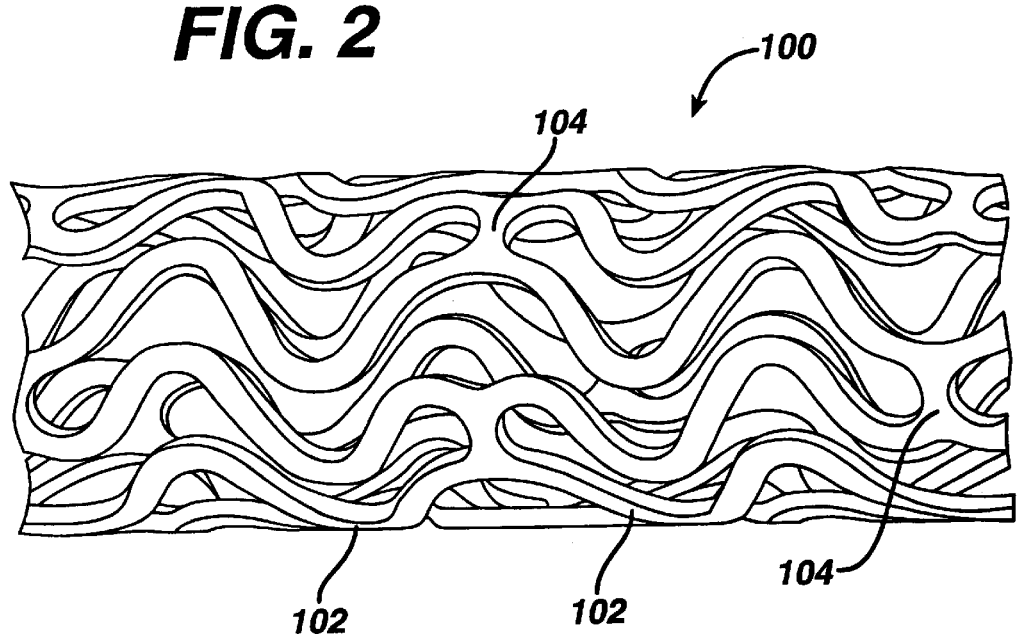
FIG. 2 is a view along the length of a stent (ends not shown) prior to expansion showing the exterior surface of the stent and the characteristic banding pattern.

FIG. 2 illustrates an exemplary stent 100 which may be utilized in accordance with an exemplary embodiment of the present invention. The expandable cylindrical stent 100 comprises a fenestrated structure for placement in a blood vessel, duct or lumen to hold the vessel, duct or lumen open, more particularly for protecting a segment of artery from restenosis after angioplasty. The stent 100 may be expanded circumferentially and maintained in an expanded configuration, that is circumferentially or radially rigid. The stent 100 is axially flexible and when flexed at a band, the stent 100 avoids any externally-protruding component parts.

The stent 100 generally comprises first and second ends with an intermediate section therebetween. The stent 100 has a longitudinal axis and comprises a plurality of longitudinally disposed bands 102, wherein each band 102 defines a generally continuous wave along a line segment parallel to the longitudinal axis. A plurality of circumferentially arranged links 104 maintain the bands 102 in a substantially tubular structure. Essentially, each longitudinally disposed band 102 is connected at a plurality of periodic locations, by a short circumferentially arranged link 104 to an adjacent band 102. The wave associated with each of the bands 102 has approximately the same fundamental spatial frequency in the intermediate section, and the bands 102 are so disposed that the wave associated with them are generally aligned so as to be generally in phase with one another. As illustrated in the figure, each longitudinally arranged band 102 undulates through approximately two cycles before there is a link to an adjacent band.

The stent 100 may be fabricated utilizing any number of methods. For example, the stent 100 may be fabricated from a hollow or formed stainless steel tube that may be machined using lasers, electric discharge milling, chemical etching or other means. The stent 100 is inserted into the body and placed at the desired site in an unexpanded form. In one embodiment, expansion may be effected in a blood vessel by a balloon catheter, where the final diameter of the stent 100 is a function of the diameter of the balloon catheter used.

It should be appreciated that a stent 100 in accordance with the present invention may be embodied in a shape-memory material, including, for example, an appropriate alloy of nickel and titanium. In this embodiment, after the stent 100 has been formed it may be compressed so as to occupy a space sufficiently small as to permit its insertion in a blood vessel or other tissue by insertion means, wherein the insertion means include a suitable catheter, or flexible rod. On emerging from the catheter, the stent 100 may be configured to expand into the desired configuration where the expansion is automatic or triggered by a change in pressure, temperature or electrical stimulation.

Figure 3:
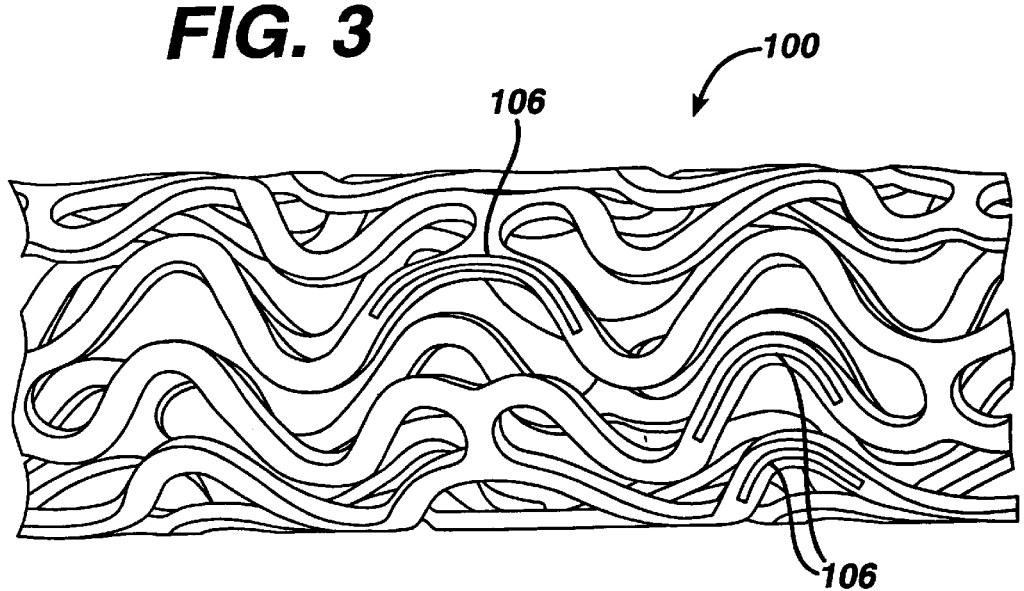
FIG. 3 is a perspective view of the stent of FIG. 1 having reservoirs in accordance with the present invention.

FIG. 3 illustrates an exemplary embodiment of the present invention utilizing the stent 100 illustrated in FIG. 2. As illustrated, the stent 100 may be modified to comprise a reservoir 106. Each of the reservoirs may be opened or closed as desired. These reservoirs 106 may be specifically designed to hold the drug, agent, compound or combinations thereof to be delivered. Regardless of the design of the stent 100, it is preferable to have the drug, agent, compound or combinations thereof dosage applied with enough specificity and a sufficient concentration to provide an effective dosage in the lesion area. In this regard, the reservoir size in the bands 102 is preferably sized to adequately apply the drug/drug combination dosage at the desired location and in the desired amount.

In an alternate exemplary embodiment, the entire inner and outer surface of the stent 100 may be coated with various drug and drug combinations in therapeutic dosage amounts. A detailed description of exemplary coating techniques is described below.

Rapamycin or any of the drugs, agents or compounds described above may be incorporated into or affixed to the stent in a number of ways and utilizing any number of biocompatible materials. In the exemplary embodiment, the rapamycin is directly incorporated into a polymeric matrix and sprayed onto the outer surface of the stent. The rapamycin elutes from the polymeric matrix over time and enters the surrounding tissue. The rapamycin preferably remains on the stent for at least three days up to approximately six months and more preferably between seven and thirty days.

Any number of non-erodible polymers may be utilized in conjunction with rapamycin. In the exemplary embodiment, the polymeric matrix comprises two layers. The base layer comprises a solution of ethylene-co-vinylacetate and polybutylmethacrylate. The rapamycin is incorporated into this layer. The outer layer comprises only polybutylmethacrylate and acts as a diffusion barrier to prevent the rapamycin from eluting too quickly and entering the surrounding tissues. The thickness of the outer layer or top coat determines the rate at which the rapamycin elutes from the matrix. Essentially, the rapamycin elutes from the matrix by diffusion through the polymer molecules. Polymers are permeable, thereby allowing solids, liquids and gases to escape therefrom. The total thickness of the polymeric matrix is in the range from about 1 micron to about 20 microns or greater.

The ethylene-co-vinylacetate, polybutylmethacrylate and rapamycin solution may be incorporated into or onto the stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved.

Since rapamycin works by entering the surrounding tissue, it is preferably only affixed to the surface of the stent making contact with one tissue. Typically, only the outer surface of the stent makes contact with the tissue. Accordingly, in a preferred embodiment, only the outer surface of the stent is coated with rapamycin. For other drugs, agents or compounds, the entire stent may be coated.

It is important to note that different polymers may be utilized for different stents. For example, in the above-described embodiment, ethylene-co-vinylacetate and polybutylmethacrylate are utilized to form the polymeric matrix. This matrix works well with stainless steel stents. Other polymers may be utilized more effectively with stents formed from other materials, including materials that exhibit superelastic properties such as alloys of nickel and titanium.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for the treatment of intimal hyperplasia in vessel walls comprising the controlled delivery, by release, for a sustained period of time in the range from about two to about six weeks, from an implantable intraluminal medical device, of an anti-inflammatory agent in therapeutic dosage amounts, the anti-inflammatory agent comprises analogs and congeners that bind a high affinity cytosolic protein, FKBP 12 and possesses the same pharmacologic properties as rapamycin.

2. Method for the treatment of intimal hyperplasia in vessel walls according to claim 1, wherein the anti-inflammatory agent reduces inflammatory cytokine levels in vascular tissues.

3. The method for the treatment of intimal hyperplasia in vessel walls according to claim 1, wherein the anti-inflammatory agent reduces monocyte chemotactic protein levels in vascular tissues.

4. The method for treatment of intimal hyperplasia in vessel walls according to claim 1, wherein the anti-inflammatory agent comprises rapamycin.

5. A drug delivery device comprising:
an implantable intraluminal medical device; and
a therapeutic dosage of an agent releasably affixed to the implantable intraluminal medical device for the treatment of inflammation caused by injury, the agent being released for a sustained period of time in the range from about two to about six weeks, the anti-inflammatory agent comprises analogs and congeners that bind a high affinity cytosolic protein, FKBP 12 and posses the same pharmacologic properties as rapamycin.

6. The drug delivery device according to claim 5, wherein the agent reduces inflammatory cytokine levels in vascular tissue.

7. The drug delivery device according to claim 5, wherein the agent reduces monocyte chemotactic protein levels in vascular tissues.

8. The drug delivery device according to claim 5, wherein the agent comprises rapamycin.

9. The drug delivery device according to claim 5, wherein the intraluminal medical device comprises a stent.

10. The drug delivery device according to claim 9, wherein the agent is incorporated in a non-erodible polymeric matrix coating affixed to the stent.

11. A method for the treatment of inflammation in vessel walls comprising the controlled delivery, by release, for a sustained period of time in the range from about two to about six weeks, from an implantable intraluminal medical device of an anti-inflammatory agent in therapeutic dosage amounts, the anti-inflammatory agent comprises analogs and congeners that bind a high affinity cytosolic protein, FKBP 12 and posses the same pharmacologic properties as rapamycin.

* * * * *